(12) United States Patent  (10) Patent No.: US 7,835,925 B2
Roe et al.                  (45) Date of Patent:    Nov. 16, 2010

(54) SYSTEM FOR IMPROVING THE MANAGEMENT OF THE HEALTH OF AN INDIVIDUAL AND RELATED METHODS

(75) Inventors: Donald C. Roe, West Chester, OH (US); Frank H. Bakes, Cincinnati, OH (US); Jonathan G. Beers, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1195 days.

(21) Appl. No.: 10/078,042

(22) Filed: Feb. 19, 2002

(65) Prior Publication Data

US 2002/0156654 A1    Oct. 24, 2002

Related U.S. Application Data

(60) Provisional application No. 60/270,025, filed on Feb. 20, 2001.

(51) Int. Cl.
    G06Q 10/00    (2006.01)
(52) U.S. Cl. .............................. 705/3; 705/2; 600/300; 600/301
(58) Field of Classification Search ................. 705/2–4; 600/300–301
    See application file for complete search history.

(56) References Cited

U.S. PATENT DOCUMENTS

| 4,448,203 | A | * | 5/1984 | Williamson et al. | ......... 600/546 |
| 5,077,666 | A | | 12/1991 | Brimm et al. | |
| 5,199,439 | A | | 4/1993 | Zimmerman et al. | |
| 5,291,400 | A | * | 3/1994 | Gilham | ....... 600/509 |
| 5,357,427 | A | | 10/1994 | Langen et al. | |
| 5,464,012 | A | * | 11/1995 | Falcone | ....... 600/301 |
| 5,515,865 | A | | 5/1996 | Scanlon | |
| 5,549,117 | A | | 8/1996 | Tacklind et al. | |
| 5,558,638 | A | | 9/1996 | Evers et al. | |
| 5,576,952 | A | | 11/1996 | Stutman et al. | |
| 5,671,734 | A | | 9/1997 | Pugh | |
| 5,704,366 | A | | 1/1998 | Tacklind et al. | |
| 5,732,709 | A | | 3/1998 | Tacklind et al. | |
| 5,778,882 | A | | 7/1998 | Raymond et al. | |
| 5,828,751 | A | * | 10/1998 | Walker et al. | ............... 713/175 |
| 5,832,448 | A | | 11/1998 | Brown | |
| 5,897,493 | A | | 4/1999 | Brown | |
| 5,920,478 | A | * | 7/1999 | Ekblad et al. | ................. 700/29 |
| 5,941,820 | A | | 8/1999 | Zimmerman | |
| 5,956,689 | A | | 9/1999 | Everhart, III | |
| 5,974,124 | A | | 10/1999 | Schlueter, Jr. et al. | |
| 6,055,506 | A | * | 4/2000 | Frasca, Jr. | ..................... 705/3 |
| 6,093,146 | A | * | 7/2000 | Filangeri | .................... 600/300 |
| 6,283,923 | B1 | * | 9/2001 | Finkelstein et al. | ......... 600/532 |
| 6,319,199 | B1 | * | 11/2001 | Sheehan et al. | ............. 600/200 |
| 6,540,674 | B2 | * | 4/2003 | Zadrozny et al. | ............ 600/300 |
| 6,643,592 | B1 | * | 11/2003 | Loman et al. | ................. 702/35 |
| 6,658,287 | B1 | * | 12/2003 | Litt et al. | ..................... 600/544 |
| 6,936,007 | B2 | * | 8/2005 | Quy | ........................... 600/300 |
| 2006/0015370 | A1 | * | 1/2006 | Shen | ............................. 705/2 |
| 2006/0161457 | A1 | * | 7/2006 | Rapaport et al. | ............... 705/2 |

* cited by examiner

Primary Examiner—Vivek D Koppikar
(74) Attorney, Agent, or Firm—Kenneth K. Patel; Thibault Fayette; William E. Gallagher

(57) ABSTRACT

A system and associated methods for improving the management of an individual's health is provided. The system includes a data measurement mechanism generating information relevant to a particular health condition, a data acquisition mechanism for transferring the information to a storage medium, at least one data analysis mechanism generating insights relevant to a particular health condition and an information presentation mechanism for displaying the insights to a patient, caregiver or physician.

6 Claims, 7 Drawing Sheets

SYSTEM FOR IMPROVING THE MANAGEMENT OF THE HEALTH OF AN INDIVIDUAL AND RELATED METHODS

CROSS REFERENCE TO RELATED APPLICATION

This application claims the benefit of U.S. Provisional Application No. 60/270,025, filed Feb. 20, 2001.

FIELD OF THE INVENTION

The present invention relates to a system, and associated methods utilizing data measurement, acquisition, and analysis techniques facilitating the management and/or improvement of an individual's health.

BACKGROUND OF THE INVENTION

For purposes of health maintenance, medical diagnosis and treatment, the human body may be treated as a process or a set of inter-related processes. Use of quantitative (e.g., measured) and qualitative (e.g., observed) data to assess the health of an individual is a critical element in current medical diagnostic and monitoring practice. A wide range of measurement tools are made available to the general public and the medical profession designed to provide quantitative data on medically relevant health parameters, such as body temperature, pulse, respiration rate, blood oxygen content, and blood glucose levels, among others. Certain measurements may be obtained using sensors, some of which may be attached to the body for continual data generation, such as EKG and pulse oximetry sensors. Additionally, qualitative observations are obtained via visual examination, questionnaires, and interaction with the individual or patient.

Data is acquired (i.e., put into a storage or analysis medium or device) in a number of ways, including manual entry of data onto charts or into computer systems or automatic electronic transmission of data from sensors to a computer database or system. The art reveals that an attempt has been made to use a remote querying device to request and obtain data from remotely located patients. Additionally, a system used to measure cardio-pulmonary data and download it to an Internet website for analysis and review by physicians has been described.

Attempts have also been made in the art to apply statistical control theory, including control chart techniques, to quantitative measurements of health parameters for the purpose of identifying changes in the "process" (i.e., the health of the patient) that require medical intervention. Attempts have additionally been made to provide visual representations of medical data in the form of graphs or descriptive icons. Although the tools available in the art for monitoring health facilitate diagnosis and treatment of health conditions, for the most part the tools are either too complex for use or are too technical to be understood by the general public.

Thus, there is a need for a user-friendly health monitoring system capable of providing sufficient diagnostic analyses of various medical conditions or health related events. In addition, there is a need for system capable of comparing relevant population data for the purposes of identifying or selecting potentially relevant causes or remedies addressing particular health conditions. Finally, there is a need for a health monitoring system capable of predicting and/or preventing future occurrences of medical conditions or health events.

SUMMARY OF THE INVENTION

The present invention addresses the limitations of the prior art by providing a system and associated methods to improve the management of an individual's health. The system includes a data measurement mechanism generating data relevant to a particular health condition and a data acquisition mechanism for transferring the relevant data to a storage medium. In addition, the system includes and at least one data analysis mechanism generating insights relevant to a particular health condition and an information presentation mechanism for displaying the insights relevant to the particular health condition to a patient, caregiver or physician. The analysis performed by the data analysis mechanism can include population comparison, multi-variate analysis, attribute data analysis, and reliability engineering analysis.

BRIEF DESCRIPTION OF THE DRAWINGS

While the specification concludes with claims particularly pointing out and distinctly claiming the subject matter that is regarded as the present invention, it is believed that the description will be better understood from the following descriptions that are taken in conjunction with the accompanying drawings in which like designations are used to designate substantially identical elements.

DETAILED DESCRIPTION OF THE INVENTION

Figure 1:
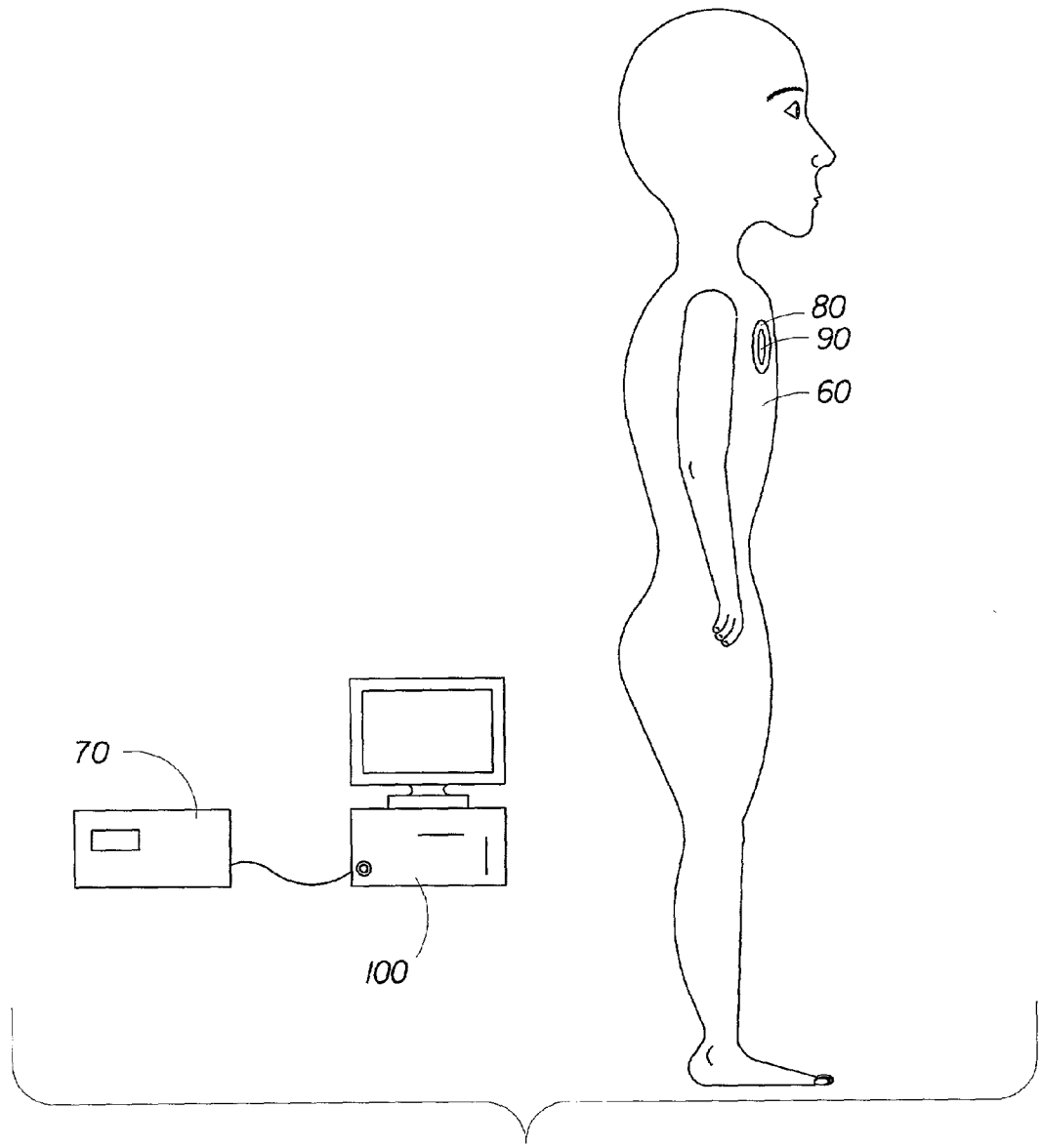
FIG. 1 illustrates an exemplary telemetry-based data measurement system.

The present invention comprises a system and related methods for facilitating the management and/or improvement of the health of at least one individual. The system is applicable to medical conditions currently known to an individual or health events that may be experienced by an individual. The system may include components or mechanisms for data measurement, data acquisition, data analysis, and presentation of information, as well as systems facilitating communication between the user and the system and/or between any or all of its components. It is envisioned that two or more of any or all of the above mechanisms may be employed in the health improvement system of the present invention. In certain other embodiments, any of the above mechanisms may perform the function of one or more of the other mechanisms. For example, the data acquisition mechanism may additionally perform a portion or all of the data analysis. Similarly, any device or system component of the system(s) of the present invention may perform more than one of the functions of data measurement, acquisition, analysis, and information presentation or may perform at least one of these functions while additionally performing another related function, such as data storage.

As previously stated, the system(s) of the present invention are useful in facilitating the management and/or improvement of the management of an individual's health. In particular, embodiments of the system of the present invention are useful in improving the selection and/or definition of a treatment and/or improving the evaluation of various treatments for a medical condition or health event. For example, the systems of the present invention may enable improved response (i.e., in terms of speed or specificity of treatment) of the individual or medical professional to significant changes in the individual's health parameters and/or improved evaluation of given courses of treatment. Data analysis mechanisms useful in selecting treatment include multi-variate analysis, reliability engineering techniques such as failure cause and remedy analysis, and population comparisons or population experience related to the specific medical condition or health event.

As used herein, the term "medical condition" refers to chronic, recurring, or long-term diseases or other health or development-related physical conditions such as diabetes, asthma, sleep apnea, high blood pressure, high cholesterol, cardiac problems, and the like. As used herein, the term "health parameter" refers to any observable measure, symptom, or description of the health or medical status of an individual and may be quantitative or qualitative. As used herein, the term "health event" refers to acute disease states or physical conditions, such as illnesses and injuries, as well as "flare-ups" of chronic diseases (e.g., instances where the chronic disease is "out-of-control" or presents acute symptoms).

Improvement of health, also referred to herein as "health improvement," means the reduction in the frequency, duration, or severity of an illness or other health event, the control of a chronic medical condition, the diagnosis and treatment of chronic or acute medical conditions, and/or the prevention of fixture medical conditions or health events. Additionally, health improvement may involve the assessment of efficacy of a given treatment or the comparison of an individual's medical or developmental status versus a comparable population. The system of the present invention may facilitate the management or improvement of health by supplying the individual and/or physician with information related to the diagnosis, treatments, population and/or historical comparisons, or other interventions as described herein. Regardless of the information provided, it is generally recommended for an individual to consult a physician regarding the diagnosis or treatment of a medical condition or health event. Preferably, the individual will work with the physician in advance to develop a treatment or response plan to be followed by an individual prior to the receipt of certain pre-defined signals, data, or alarm conditions.

"Data measurement", as used herein, refers to the generation of quantitative data from an individual or the generation of qualitative data (e.g., an observation) by an observer or the patient. As used herein, a "data measurement mechanism" refers to any device, system, tool, observation, visual or digital image comparison to a defined standard such as a picture, color chart, or template, or any other process by which quantitative or qualitative data is generated.

Quantitative data may include numerical readings of health parameters such as respiration rate and volume, peak airflow measurements, pulse, blood pressure, other measurable cardiopulmonary parameters as known in the art, body temperature, blood oxygen content, blood glucose levels, and levels of various biological or non-biological components of bodily exudates such as urine, feces, sweat, mucous, and saliva. Such numerical readings can be obtained via manual tools such as thermometers or blood pressure cuffs, lab assays such as blood, urine, or stool tests, or automatic tools such as sensors like those used in pulse-oximetry and cardio-pulmonary function. Qualitative data may include observations of health parameters such as muscle tone, activity, skin coloration, bowel frequency and consistency. Such observations may be obtained visually by a medical professional or by questionnaire such as that described by C. J. Morley, et al, in "Baby Check: a scoring system to grade the severity of acute systemic illness in babies under 6 months old", *Archives of Disease in Childhood,* 1991; 66;100-106, shown in Tables 1 and 2 below, and hereby incorporated by reference.

TABLE I

Score each item according to the exact wording of the question. Only score if an item is definitely present. The baby can be rescored at any time to assess changes in severity of the illness.
Have these symptoms been present in the last 24 hours?

| Score | | |
|---|---|---|
| (1) | Has the baby vomited at least half the feed after each of the last three feeds? | 4 |
| (2) | Has the baby had any bile stained (green) vomiting? 3 | 1 |
| (3) | Has the baby taken less fluids than usual in the last 24 hours? If so, score for the total amount of fluids taken as follows: | |
| | Taken only slightly less than usual (more than two-thirds of usual intake) | 3 |
| | Taken about half the usual amount (between one third and two thirds of usual intake) | 4 |
| | Taken very little (less than one third of usual intake) Breast feeding mothers should estimate the amount taken. Fluids that have been vomited should still be scored. | 9 |
| (4) | Has the baby passed less urine than usual? | 3 |
| (5) | Has there been any frank blood (not streaks) mixed with the baby's stools? 1 | 1 |
| (6) | Has the baby been drowsy (less alert than usual) when awake? If so, score as follows: | |
| | Occasionally drowsy (but usually alert) | 3 |
| | Drowsy most of the time (occasionally alert) Do not score irritability or increased sleeping | 5 |
| (7) | Has the baby had an unusual cry (sounds unusual to mother)? | 2 |
| Now examine the baby awake | | |
| (8) | Is the baby more floppy than you would expect? | 4 |
| (9) | Talk to the baby. Is the baby watching you less than you expect? | 4 |
| (10) | Is the baby wheezing (not snuffles or upper respiratory noises) on expiration? | 3 |
| (11) | Is the baby responding less than you would expect to what is going on around? | 5 |
| Now examine the baby naked for the following checks | | |
| (12) | Is there any indrawing (recession) of the lower ribs, sternum, or upper abdomen? If so, score as follows: | |
| | just visible with each breath? | 4 |
| | obvious and deep indrawing with each breath? 5 | 1 |
| (13) | Is the baby abnormally pale or has the baby looked very pale in the last 24 hours? | 3 |
| (14) | Does the baby have blue fingernails or toenails? | 3 |
| (15) | Squeeze the big toe to make it white. Release and observe colour for 3 seconds. Score if the toe is not pink within 3 seconds or if it was completely white to begin with. | 3 |
| (16) | Has the baby got an inguinal hernia? 3 | 1 |
| (17) | Has the baby an obvious generalised trunkal rash or a sore weeping rash covering an area greater than 5 × 5 cm? | 4 |
| (18) | Is the baby's rectal temperature 38.3° C. or more? | 4 |
| (19) | Has the baby cried (more than just a grizzle) during this assessment? | 3 |
| | Total Score . . . | |

TABLE II

| | |
|---|---|
| Score 0 to 7 | Your baby is well or only a little unwell and is not likely to need medical attention now. |
| Score 8 to 12 | Your baby is unwell, but is not likely to be seriously ill at the moment. Contact you doctor, health visitor, or midwife for advice. Watch your baby closely: if you think your baby is worse, do the score again. |
| Score 13 to 19 | Your baby is ill and needs to be seen by a doctor. Contact your doctor now and arrange for your baby to be seen. |
| Score 20+ | Your baby may be seriously ill and needs to be seen by a doctor straight away. |

Sensors useful in the present invention may include any sensor described for measuring or detecting a medically relevant health parameter or event or a medical condition. In certain preferred embodiments, the sensor is wearable by the individual and is monitored in an unobtrusive manner. For example, the sensor may be attached to, or part of, the individual's clothing or may be a separately applied element (e.g., a wrist or ankle band, a finger or toe ring, an adhesive patch, etc.). Any sensor as known in the art that measures or detects a medically relevant parameter may be used in the present invention, including commercially available EMG and EKG sensors, pulse oximetery sensors, temperature sensors, blood glucose sensors, spirometers, biosensors, pressure sensors, piezoelectric sensors, sound-detecting sensors, microphones, motion detecting sensors, inductive sensors, and the like. An exemplary suitable sensor system for measuring pulse rate and blood oxygen content is available as the Vitalmax 540 Pace pulse oximeter from Pace Tech Medical Monitors, Inc. of Clearwater, Fla. A suitable sensor for measuring blood glucose is available as the GlucoWatch® biographer from Cygnus, Inc. of Redwood City, Calif. A suitable spirometer is available as AirWatch from Lifechart.com of Mountain View, Calif. Additional suitable sensors are described in (SEE DMW) (include reference to sensor/responsive system apps).

In certain embodiments, the sensor can be telemetry-based, such that it communicates with a remote data acquisition system without the need for a physical connection such as a wire. The telemetry system may communicate via infrared, ultrasonic, or radio frequency (rf) transmission of the data to a data acquisition device or other data collection system or a signaling mechanism. For telemetry based systems, the sensor may include an integral power source or it may be powered by electricity generated by induction from a remote electromagnetic or rf field. An exemplary telemetry system for measuring temperature is available as the Cable Free™ Thermometer Model EMR-812A or Model JTR-168LR from the Oregon Scientific Co. of Tualatin, Oreg. Another commercially available telemetry based system is available as the AngelCare baby monitor from the Safety 1$^{st}$ Company of Chestnut Hill, Mass. In addition, a telemetry based baby monitor capable of measuring and transmitting respiration rate is described in U.S. Pat. 5,515,865.

A non-limiting embodiment of an exemplary telemetry-based data measurement system is shown in FIG. 1. In this embodiment, at least one sensor 90 measuring pulse rate, respiration rate, blood oxygen content, and/or body temperature is mounted on an adhesive patch 80 affixed to the individual's skin 60. Alternatively, the sensor(s) may be incorporated into a bracelet, anklet, sock, finger cot, or bed pad. The sensors may be powered by rf induction via a radio field generated by a baby monitor or receiver device 70. Alternatively, the sensor may be powered by a battery, preferably with at least a 12 hour life. Data is sent at a specific interval to a receiver 70 connected to desktop PC 100 functioning as a data acquisition unit. The data may be analyzed on the PC or transmitted to an Internet site for analysis. Alarm conditions, status reports, summary screens, etc., may be signaled at the PC or another device in the local environment (e.g., the individual's home) and/or may be sent to a physician. If necessary, the system can be arranged such that different information and/or alarms signaling different medical issues may be sent to different physicians.

Quantitative measurements of health or environmental parameters are referred to herein as "variables", while qualitative observations are referred to as "attribute" data. Variables may include any measured numerical data related to a health event, medical condition, the individual's demographics, or environmental or other data such as dietary components and ambient conditions (e.g., temperature, barometric pressure, pollen and mold counts, smog or other air pollution data, and the like). Attributes may include qualitative ratings, questionnaire responses, visual images (e.g., digital images), causes of a health event or medical condition, remedies or treatments for a health event or medical condition, environmental or other potentially relevant information, such as diet, activity, and medical history. Attributes may also include demographic data. Demographics may comprise variables and attributes including an individual's age, gender, race, geographical location, medical history, current medical conditions, symptoms, or health events, vocation, stress factors, psychographic or temperament data, and any other descriptive information related to the individual, their family, or environment.

For some medical conditions it may be necessary to monitor both variables and attributes. For example, an asthmatic typically keeps track of variables such as quantitative pulmonary function data such as peak expiratory flow rate. However, asthmatic conditions may also be affected by environmental influences. Therefore, an asthmatic may also record attribute data such as pollen or mold count, weather conditions (e.g., rain, cold temperatures, sudden weather changes, barometric pressure changes, etc.), activity level (e.g., exercise), environmental factors (e.g., exposure to pets, smokers, dust, etc.), prophylactic or remedial treatments such as the use of oral steroids or bronchdilators, and/or symptoms such as wheezing, or retraction. This data may be used to identify asthma attack triggers and ultimately predict when asthma events are more likely to occur, facilitating an improved prophylactic treatment plan in conjunction with the asthmatic's physician.

Attribute data may be manually recorded or may be input into an electronic spirometer, such as a device similar to the above-mentioned AirWatch device, via a touch screen or picklists. If the data comprises a visual image, then the image may be subjected to subsequent quantitative or objective analyses (e.g., color analysis, size/geometry, etc.) or trained medical personnel may grade the image. For example, an otoscope device may be fitted with a CCD digital image capture chip to capture images of the external surface of the tympanum and surrounding tissues for review by a physician to facilitate diagnosis of acute otitis media. The images may be transmitted for viewing or analysis at remote locations via phone lines, e-mail, or an Internet web site. In addition, the color of the tympanic membrane may be measured and compared to the individual's historical data or to population data to facilitate diagnosis.

A digital image capture device, such as a digital image otoscope, may include fiber optics for light and/or image transmission to facilitate the design of a small tip which is insertable into the ear canal. Preferably the digital image capture device is a handheld unit comprising a main body adapted to be held by a human hand, at least one light source, a power source (e.g., disposable or rechargeable batteries), an image acquisition tip, at least one image capture chip or sensor (e.g., CCD or CMOS chips) or a digital camera, at least one data transmission port (e.g., a phone jack, USB port, serial port, parallel port, etc.), at least one electronic data storage mechanism (e.g., floppy disk, data chip, "memory stick", hard drive, CD-ROM, or any other data or image storage element known in the art), and any associated electronics. The image acquisition tip is adapted to easily fit into the ear canal and provide line-of-sight access to the tympanic membrane. The image acquisition tip may be in the form of a standard speculum and may be made of rigid or conformable materials. In one embodiment, the tip is customizable for a given individual. The tip may be at least partially disposable. Exemplary image capture chips and sensors include CCD chips available from Kodak of Rochester, N.Y., as KAF-2001CE, KAF-3000CE, KAF-5100CE, KAF-6302CE, KAF-16801CE, KAI-0311M, KAI-0372M, KAI-1003M, and KAI-1010M and from Texas Instruments, Inc. of Dallas, Tex., as TC213 and TC281. Also suitable are CMOS image sensors available from Kodak as KAC-1310. Additionally, suitable color board cameras are available as MTV-5361, MTV-5317, MTV-5311, MTV-5364, MTV-5360, MTV-5366, MTV-5367, and MTV-5384 from Mintron Enterprise USA of Fremont, Calif.

Attributes may be adapted to be treated as variables or pseudo-variables by assigning numerical point values, codes, or ratings to various states of the attribute. For example, in a non-limiting embodiment, skin rashes may be qualitatively scored as "none", "slight erythema", "moderate erythema", "severe erythema", "localized edema", "widespread edema", and "bloody edema" in a progression of severity, from least to most. A numerical rating may be assigned to each level of rash, starting with "0" for "none" and leading to "6" for "bloody edema". The numerical ratings may be used in subsequent qualitative statistical analyses as described below for variable data. Alternatively, a point value may be assigned to each attribute within a related group, such as in the "Baby Check" scorecard described above. In this case, the cumulative score from the entire set of related attributes may become a single variable representing at least a portion of the health status of an individual.

In certain embodiments of the present invention, data may be recorded, stored, analyzed, and interpreted as it is measured or observed (e.g., measurements of body temperature or observations of blood in the stool). In other embodiments, the data may be used (recorded, stored, analyzed, interpreted etc.) as actually collected or recorded, but may differ from the actual measurement taken. For example, a "difference", such as a deviation from the previous measurement or observation, may be recorded in addition to, or in place of, the actual measurement of a health parameter. In alternative embodiments, the data may be used (recorded, stored, analyzed, interpreted etc.) after a mathematical calculation or transformation. For example, an average, moving average, range, standard deviation, log value, exponential value, weighted value, normalized values, ratios, sums, and other mathematical transformations or derivations may be used as data useful in facilitating the management and/or improvement of the health of an individual.

The time or frequency of data measurement, or sampling strategy, is also important in certain embodiments of the present invention. "Sampling strategy" refers to the choice(s) or plan for the frequency and timing and method for data measurement. Typically, the sampling strategy is based on a frequency and timing that provides actionable data enabling the individual to control the medical condition or health event. Sampling strategy may also be determined by the desire to reduce "noise" or unwanted variation in the data. For example, a diabetic may measure their blood glucose level only immediately prior to a meal in order to reduce variation and provide the ability to "act" on the data before eating. In another non-limiting example, sampling of an infant's respiration rate may, in some cases, only be done during the night while the infant and caregiver are sleeping. Further, routine measurement of data for health event screening may be done only at a specific time of the day or may be done randomly. For example, body weight and temperature vary in known and predictable patterns throughout the day and may be measured, in some applications, at the same time of each day to minimize variation.

Once data is produced or available, it is preferably entered into a storage device or system for analysis via a data acquisition mechanism. "Data acquisition", as used herein, refers to the step of transferring the data from its source or initially recorded location to a data storage medium or system, such as a handheld device, personal computer (PC), mainframe computer, local area network (LAN) server, or an Internet website. A "data acquisition mechanism" refers to any device, system, or process capable of transferring data to the storage medium or system. In certain embodiments of the present invention, the data measurement mechanism may perform the data acquisition function such as in the case of a telemetry-based sensor, which may transmit the measurements directly to a PC or other storage system.

The data acquisition mechanism may comprise a handheld device. The handheld device may be a handheld PC or a personal digital assistant (PDA), such as a Palm IV or V, available from the 3Com Corporation of Santa Clara, Calif. Data may be electronically entered into the handheld device, such as from a sensor or data logger, or the data may be manually entered. The handheld device may also comprise a "tablet PC" mobile computer such as the Cassiopeia FIVA Tablet available from the Casio Computer Co., Ltd. of Tokyo, Japan, or the Stylistic LT pen tablet computer available from Fujitsu Personal Systems, Inc. of Santa Clara, Calif. Data entry into a tablet PC may be accomplished via the touch screen, integrated keypad, a wireless keyboard, or a microphone. Data residing in the data acquisition mechanism may be downloaded to a PC or to an Internet website or any other storage system. For example, the previously mentioned AirWatch spirometer stores a limited number of data points, which may be automatically downloaded from the device to an Internet website, via a telephone connection, to be available to the user, caregiver, or physician. This data is preferably made available, on a PC or website, for analysis via Quality Window software as described herein. For example, control charts of PEF and FEVI using statistically derived control limits have proven useful in understanding the status, and triggers of an individual's asthma as well as providing a statistically valid means of evaluating various treatments.

In other embodiments, the data acquisition mechanism may comprise a "wearable PC". A wearable PC may comprise a device wherein the functional components of a laptop PC, for example, are distributed within a belt, pouch, backpack, waist pack, vest, or other article of clothing or wearable storage container in an operative manner (i.e., the PC still functions). Such a system may comprise a wearable view screen (i.e., on an armband) or a pair of heads-up display glasses (laser worn over the ear displays the image on the inside of specially designed glasses) to provide "hands-free" operation.

Figure 2:
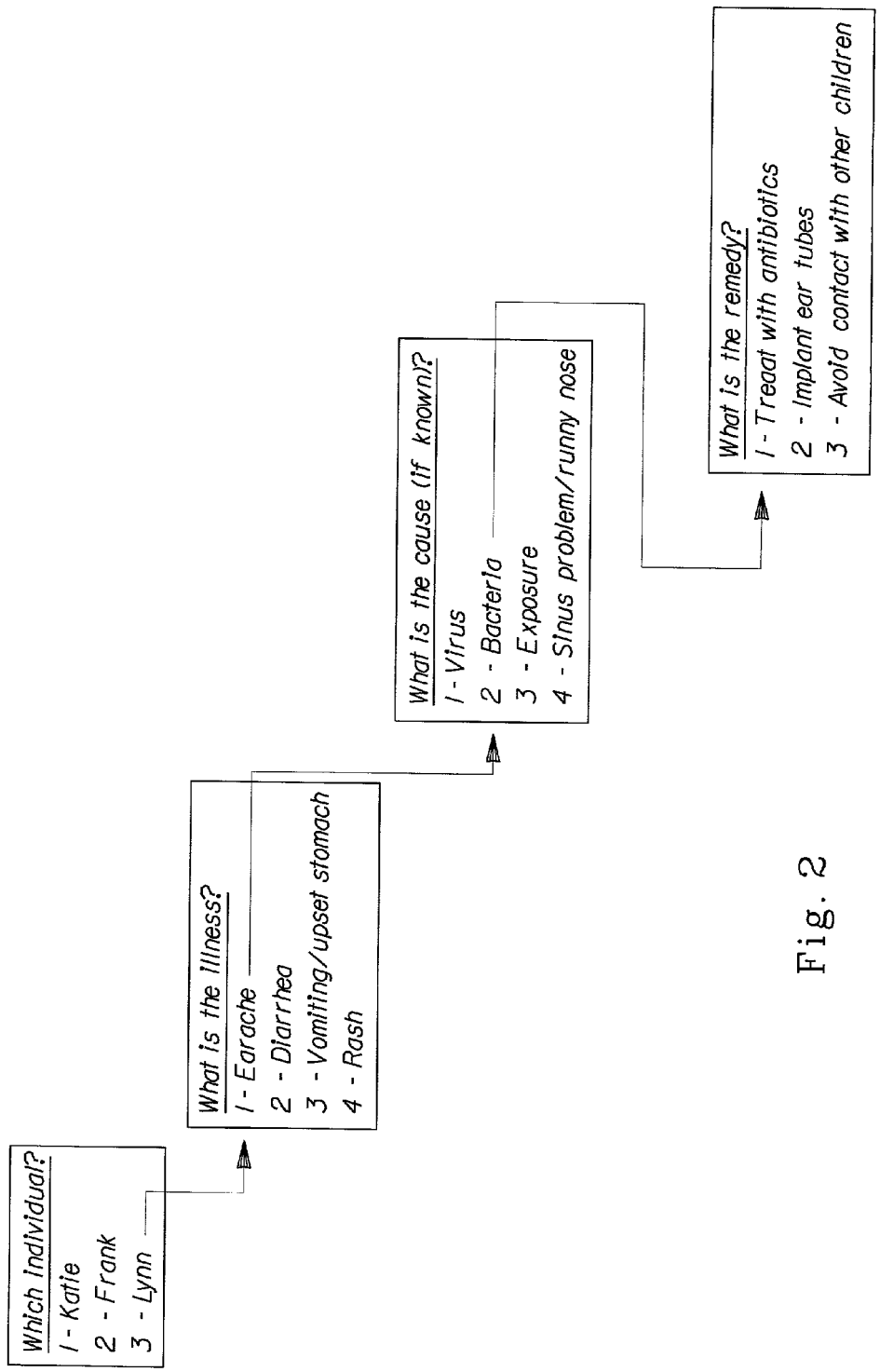
FIG. 2 illustrates a pick list for a data entry screen that enables a user to choose the most suitable choice or option from a list presented on the screen.

The data acquisition mechanism of the present invention may have a user-friendly interface facilitating manual entry of data into the system. In embodiments wherein the data acquisition mechanism comprises a PDA (or other handheld device), the PDA screen may be adapted for entry of numerical data or text data. The entry screen may comprise a graphical or icon-based selection or input interface for ease of use and understanding by the user. For the entry of attribute data such as causes of a health event, treatments or other remedies, demographic data, and the like, the data entry screen or screens preferably comprise "pick-lists" wherein the user chooses the most suitable choice or option from a list presented on the screen. In preferred embodiments, the pick lists have multiple levels (i.e., choosing one option will bring up at least a second list having a greater level of detail or specificity). FIG. 2 depicts the decision process behind an exemplary pick-list approach. Here, a specific health event selected from a linked "tree" of a general set of health events for a particular individual (Lynn) happens to involve a bacterial ear infection treated with antibiotics.

The data acquisition mechanism of the system of the present invention additionally has the capability to provide some initial level of analysis of the data. For example, the PDA may be adapted to alarm the user or medical professional that a specific health parameter is out of statistical control. Alternatively, the PDA may comprise a summary screen with an icon-based health status system. The summary screen may provide an overview of a portion or all of the quantitative and/or qualitative health parameters of interest and may highlight those, if any, which are deviating from historical or from desired ranges. Use of audio or video input or acquisition of the data is also contemplated (e.g., voice recognition, symbol recognition, scanned or digital images, etc.). For example, when data acquisition devices of sufficient computing power are used, speech recognition (i.e., speech-to-text) may be accomplished via software such as Microsoft Speech SLK, available from the Microsoft Company of Redmond, Wash.

Once acquired, the data is analyzed to determine if some level of intervention may be required. Such intervention may include medical treatment, consultation with a physician or other trained medical professional, and/or the implementation of or compliance with a previously defined treatment plan. Analysis of the data is generally performed via a data analysis mechanism. As used herein, a "data analysis mechanism" refers to any device, process, statistical analysis, graphical analysis, software, or any other analytical approach, such as graphing, charting, statistical methods, and other systems, manual and/or electronic, that may provide useful information pertaining to the health of an individual. Such useful information includes the need to intervene, assessment of the efficacy of a treatment, definition of most common or likely causes or effective remedies or treatments, or identification of other medically relevant insights or actions.

Statistical control chart techniques provide means of identifying changes in the health of an individual. The general use of control charts to control health parameters based on an individual's historical, or recent, data is described in U.S. Pat. No. 5,199,439, incorporated herein by reference. Control charts useful in the present invention include X-bar (mean) and R (Range) charts, X-bar and S (standard deviation) charts, moving average charts, individuals charts, target and limit charts (i.e., the process is controlled around a target instead of the mean), c-charts, p-charts, and any other statistical charts known in the process control art. The limits may include any statistical limits, or control limits, as known in the art (e.g., limit equals the mean or target +/−three times the average range, 2 or 3 times the standard deviation, etc.), or may be medically relevant limits (i.e., specification or "spec" limits) wherein exceeding the limit indicates a serious health issue or risk regardless of statistical limits. Control charts useful to the present invention comprise at least one limit on one side (i.e., upper or lower) of the mean or target. In certain preferred embodiments, the control chart comprises at least one limit on each side of the mean or target. In other preferred embodiments, the control chart may comprise two or more limits on one side of the mean or target. In other preferred embodiments, the control charts include at least one limit on each side of the mean or target. A suitable data analysis software is available from the Busitech Co. of Cornwall, Ontario, as the Quality Window Version 4.5 (DOS version), Quality Window XL (Windows version), or QWchart. As used herein, "Quality Window software" refers to any historical, current, or future version or derivation of the software, or substantial equivalents, described above.

Figure 3:
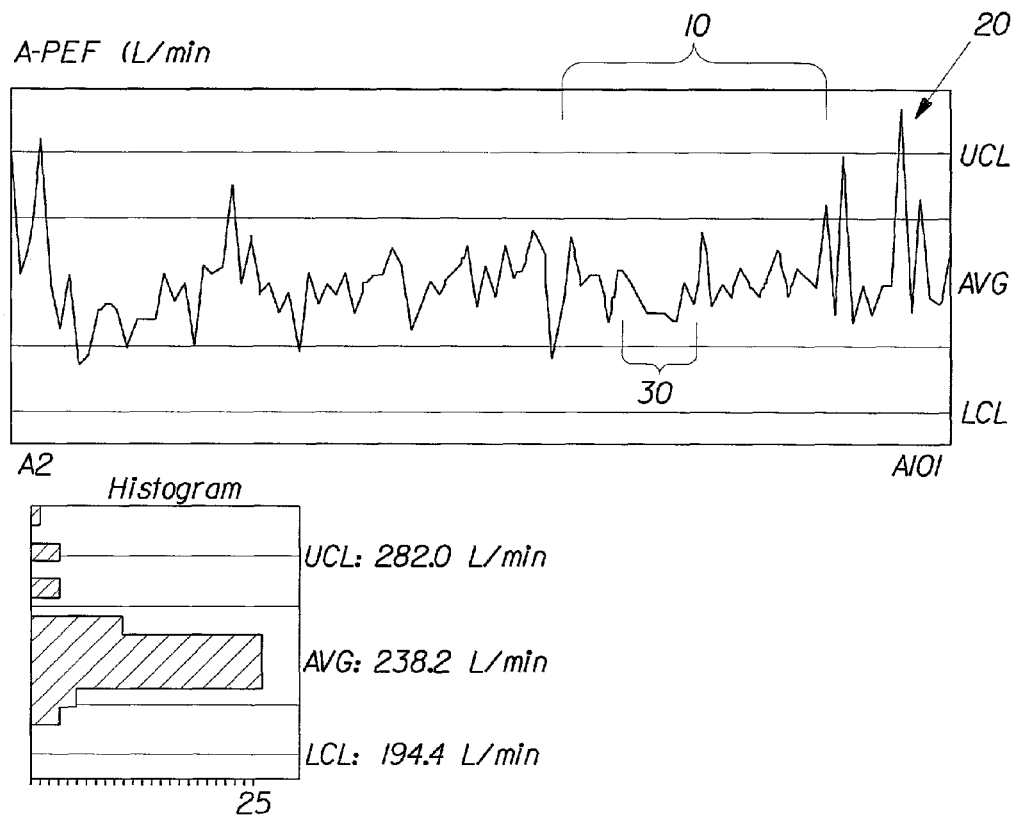
FIG. 3 depicts a control chart of peak flow measurements (PEF) of an 8-year-old asthma patient.

Statistical control limits may be calculated using historical data from the individual using any statistically meaningful group of consecutive data, such as described in U.S. Pat. No. 5,199,439 above. However, it has been found that processes such as health management may be significantly improved if the historical data used to calculate the control limits represents the "best observed" performance of the individual. The "best observed" performance of the individual may comprise a range of data representing the individual in his or her most healthy state or representing the period when an individual's medical condition was under the best-demonstrated statistical control. By choosing the "best observed" performance as the baseline, the individual and associated medical professionals are continually alerted to the possibility of better performance and have the basis for more in-depth investigation and analysis to define the factors (individual habits, environmental factors, etc.) and/or treatments critical to maintaining the "best possible" control of the health parameter or medical condition. For example, FIG. 3 depicts a control chart of peak flow measurements (PEF) of an 8 year old female having an average peak expiratory flow rate of 238.2 liters per minute (L/min) and upper and lower historical control limits of 282.0 and 194.4 L/min, respectively. The control limits may be recalculated based on the highlighted "best observed performance region" 10. The recalculated upper and lower control limits, based on average +/−three standard deviations, are 270.0 and 210.0 L/min, respectively, facilitating the management of the individual's asthma using his/her most up-to-date capability. Recalculation of control limits based on demonstrated "improved" performance increases the sensitivity of the charts to future deviations or changes. In certain preferred embodiments of the present invention, the control limits may be automatically recalculated and applied to the data at a specific interval, at the prompting of the individual or physician, or upon the achievement of a pre-defined event (i.e., a specific variation level or goal is reached).

Medically relevant limits may function similarly to "specification limits" as commonly used in product quality control in a manufacturing setting and may be set based on general medical experience, clinical research, or the experience or history of the individual. Some non-limiting examples of medical limits may include body temperatures (e.g., above 104 degrees F.), peak flow rates for an asthmatic below 100 liters/min or below 50% of the individual's historical maximum, blood sugar levels above 600 mg/dl or below 25 mg/dl, etc.

Intervention is generally indicated when health parameters fall outside of the specification limits (e.g., medical limits) or when statistically significant changes in the health parameter are identified (i.e., the process has changed). Changes in the process potentially requiring intervention by the individual, medical professional, or other caregiver may be indicated on control charts via "control rules". There are a variety of control rules in the statistical process control art, including, as non-limiting examples, points outside of control limits, runs of points more than a certain distance from the mean or target (e.g., more than 1.5 standard deviations from the mean or target), or runs of consecutive points on one side of the mean or target (e.g., 7 in a row or 10 of 11). These conditions would be indicated on the aforementioned Quality Window software by "one point in the red", "three consecutive points in the yellow", and "seven consecutive or ten of eleven consecutive points on one side of the mean or target", respectively. Any of these conditions indicate the need to intervene. FIG. 3 depicts an example of an asthmatic individual's peak flow measurements over time showing violations based on violation of control limits 20 and violation of a runs-related rule 30 (7 consecutive points on the same side of the mean). For each of these out-of-control signals indicating a statistically significant shift in the process, a medical treatment intervention, such as administration of a bronchodilator, may be indicated as previously defined by a physician.

Out-of-control situations may result from "special causes" which are outside the normal experience of the individual (e.g., an asthmatic exposed to cigarette smoke or contracting a respiratory illness) or may represent fundamental shifts in the individual or environment (e.g., an asthmatic becoming insensitive to a medication gradually over time or the asthmatic moving to a different climate). A set of control rules should be used which allow the data analysis system to identify either of these types of changes in the process requiring intervention. It is important to note that while the control rules specifically discussed herein may be preferred, any other control rules as known in the art are also applicable to health parameter data and the data analysis mechanisms of the present invention.

In certain embodiments, it is desirable to control a health parameter to a particular target, rather than to a historical mean for the individual. For example, a diabetic may want to target a particular blood sugar level or an asthmatic may target a certain peak expiratory flow. Progress or performance against the target may be indicated numerically, graphically, or via an icon or a help "guide" (described below).

The ability of the individual to remain centered on the target may be measured via a calculated parameter referred to herein as a "target-z". The target-z ($T_z$) for a defined group of data for a given parameter is calculated based on the following equation:

$$T_z = (X\text{bar} - T)/s$$

Xbar is the mean value of the parameter for the group of data, T is the defined target value of the parameter, and s is the sample standard deviation calculated by the following equation:

$$s = (\Sigma(x_i - x\text{-bar})^2/(n-1))^{1/2}$$

where $x_i$ are all of the individual data points, x-bar is the arithmetic mean of the data points, and n is the number of data points.

It is often desirable to determine whether a current treatment process or regime is capable of maintaining a given health parameter within a set of specification limits or medical limits. Capability" may be measured by $C_R$ (capability ratio) and $T_x$ (target-z). The capability ratio is a measure of how well the variation of a process "fits" within the specification limits and is calculated via the following equation:

$$C_R = 6s/(USL - LSL)$$

where s is the standard deviation as described above and USL and LSL are the upper and lower specification limits, respectively. The $T_z$ (target-z) is a measure of how well the process average is on the target and is calculated by dividing the standard deviation (s) by the mean. A process may be generally considered capable if the $C_R$ is less than or equal to 0.75 and the $T_z$ is less than or equal to 0.5.

Figure 4:
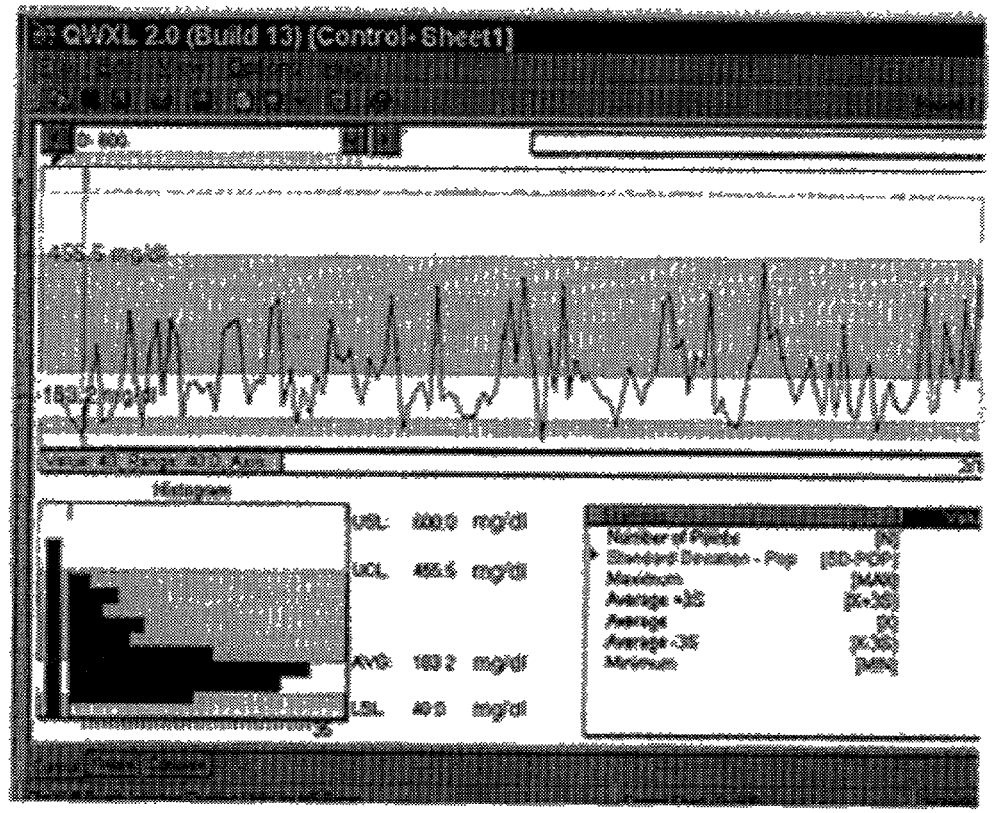
FIG. 4 depicts a control chart of 4 months of pre-dinner blood sugar data for an eight-year-old diabetic.

A non-capable health parameter for a health-related process having specification limits that are medically based requires alternative treatment approaches in order to attempt to improve the level of control over the health parameter and improve the health of the individual. For example, FIG. 4 depicts 4 months of pre-dinner blood sugar data for an eight-year-old diabetic. For the data shown, $C_R = 0.94$ and $T_z = 0.7$. Thus, the process is incapable of remaining within the doctor-specified limits of 80 and 120 mg/dl. The health parameter (i.e., blood sugar level) will continue to regularly fall outside the medical limits unless a change in the treatment regime is instituted (e.g., eating several small healthy snacks in the afternoon between lunch and dinner).

In other embodiments of the present invention, the data for an individual is compared to population data. Such data may include either the entire dataset, selected portions of the dataset, or individual points from the dataset. Comparing data for a variety of health parameters to population data is significant in order to determine how far the individual's health parameters are from established baselines or from similar groups of individuals. Population data may include all humans for which data is available or specific subgroups of the overall population particularly relevant to the individual. For example, a relevant population may comprise all male Hispanic babies living in the United States between the ages of 12 and 15 months of age. A comparison of the individual's data with multiple populations of varying specificity is often useful. One especially important use of population baseline comparisons is the assessment of a baby or child's development (e.g., height/length, weight, activity milestones, etc.). Comparisons of individual data to population data can also be useful in diagnosing specific medical conditions requiring treatment, such as diseases resulting in cranial swelling (e.g., hydrocephaly).

In the present invention, two or more health parameters may be compared using multi-variate analysis. Multi-variate analysis as applied to health parameters is useful for discovering and defining relationships between different health parameters. Health parameters may be compared using regression analysis to define correlations, ANOVA, comparison of means an/or distributions (e.g., via histograms or Pareto charts) or other descriptive statistics, and any other multi-variate analysis techniques as known in the art. While comparison of health parameters generally involve two or more types of variable data, comparisons can also be made between variable data and attribute data.

In a non-limiting example, variable data such as peak expiratory flow rate (PEFR) and forced expiratory volume in 1 second (FEVI) data for the above 8.5-year-old female asthmatic may be compared via linear regression techniques to define a potential correlation. Similarly, variable and attribute data may be compared by comparing the variable data statistics at two or more levels of the attribute(s) of interest. In these embodiments, the attribute data may be a health parameter or may be another parameter such as environmental data, diet, activity type or level of the individual, and the like. In this case, the attribute becomes a means of categorizing the variable data. For example, peak flow data for an asthmatic obtained prior to use of a bronchodilator may be compared to similar data obtained at some defined time after use of a bronchodilator to asses the efficacy of the current prophylactic treatment. Alternatively, peak flow data obtained before and after a change in weather may be compared.

The present invention also involves applying reliability-engineering theory and techniques to medical data. Reliability engineering is the study of failure in terms of cause, frequency, duration, and severity. Reliability engineering also involves identifying the cause and potential or likely remedies for the failure, so that future failures can be predicted and prevented.

Reliability engineering comprises a variety of tools, including failure analysis. As used herein, "failure analysis" refers to the recording, tracking, and assessment of the causes and potential remedies for disruptions to a process (i.e., "failures"). Failures related to an individual's health are referred to herein as health process failures or health events. Health events include, without limitation, illnesses, injuries, flare-ups or incidents of chronic medical conditions (e.g., cardiac conditions, asthma, allergic responses, out-of-control blood sugar for diabetics, high blood pressure or cholesterol, and migraines, to name a few) and other health events resulting in a change in physical well being or activity.

The timescale of the duration of the health events and/or the time between health events may be long (i.e., weeks, months, or years) or relatively short (i.e., days, hours, minutes). Health events, are tracked by recording data for each incident or event, and may include the time and/or date of the event, the duration, type, or severity of the event, the cause (i.e., known or probable, if available) of the event, and the attempted and/or successful remedies or treatments of the event. Data on failures is preferably analyzed via the process control techniques described above (e.g., control charting, etc.) for variable data. Causes and remedies of failures, such as health events, may be treated as attribute data. The Control, Relate, Compare, Prioritize, and Forecast analysis functions of the Quality Window version 4.5 software (DOS) or Quality Window XL (Windows addition to Microsoft Excel) described above are particularly useful in applying reliability engineering techniques such as failure analysis to health data.

In preferred embodiments of the present invention, the time-between-failures is analyzed, preferably via control chart, histogram, or other statistical techniques. For example, the time between asthma attacks may be analyzed and/or charted to define trends and assess the effect of various treatments. Table 3 includes data on time-between-events for an asthmatic female during her first 8.5 years of life, both before and after the introduction of a new prophylactic treatment.

TABLE 3

| | Mean Time between asthma attacks (days) |
|---|---|
| Before new treatment | 27.2 |
| After beginning new treatment | 62.3 |

Before the new treatment, the time between events was about 27 days, while after the introduction of the new treatment, the average time between events increased to about 62 days. After such a successful intervention, the mean and control limits may be recalculated as described above.

It is often useful to analyze the duration of the events, as well as the time interval between them. For example, the duration of the asthma events described above may be presented in control chart and histogram form, with associated statistics. There may, in some instances, be a period of shorter (i.e., lower duration) asthma events. Such an indication could lead a medical professional to identify the particular cause of the deviation in the population during this period and adapt the patient's treatment regime. Additionally, as above, the application of multi-variate analysis to reliability engineering data is often useful.

In addition to variable data, attribute data is also valuable in improving an individual's health using reliability engineering analysis of health processes. In embodiments wherein health event cause, remedy/treatment, and/or symptom data or other pertinent information is measured and recorded as part of the health event, the data is available to aid in the treatment and/or prevention of similar future health events. In these embodiments, the individual or medical professional can analyze the causes and/or treatments (attempted or successful) to identify the most common causes of the failure and/or the most successful remedies for the particular type of failure. For example, an asthmatic individual may learn from this analysis that the majority of failures (i.e., asthma attacks or episodes) are caused by certain weather changes including temperature and/or conditions. In this case, the treatment regime may be adjusted to prevent or reduce the severity of future attacks by increasing asthma medication when a particular type of weather change is predicted. In another non-limiting example, a caregiver or medical professional may determine via this type of analysis that ear infections in a particular patient are only resolved via a particular antibiotic and that other antibiotics are ineffective. In this case, the doctor may choose to prescribe the historically effective antibiotic first to reduce the duration of the event.

Demographic data is also often useful in failure analysis. Demographic data provides the additional capability of accessing the experiences of comparable groups of individuals for the purpose of identifying probable causes or most successful possible treatments for a given type of health event or medical condition. Application of the experiences of a large, relevant population may facilitate the identification of the most likely causes of a health event, and/or remedies for the health event where the cause is not known for a particular individual. This information may then be used to more efficiently identify particular treatment options with less trial-and-error.

Figure 5:
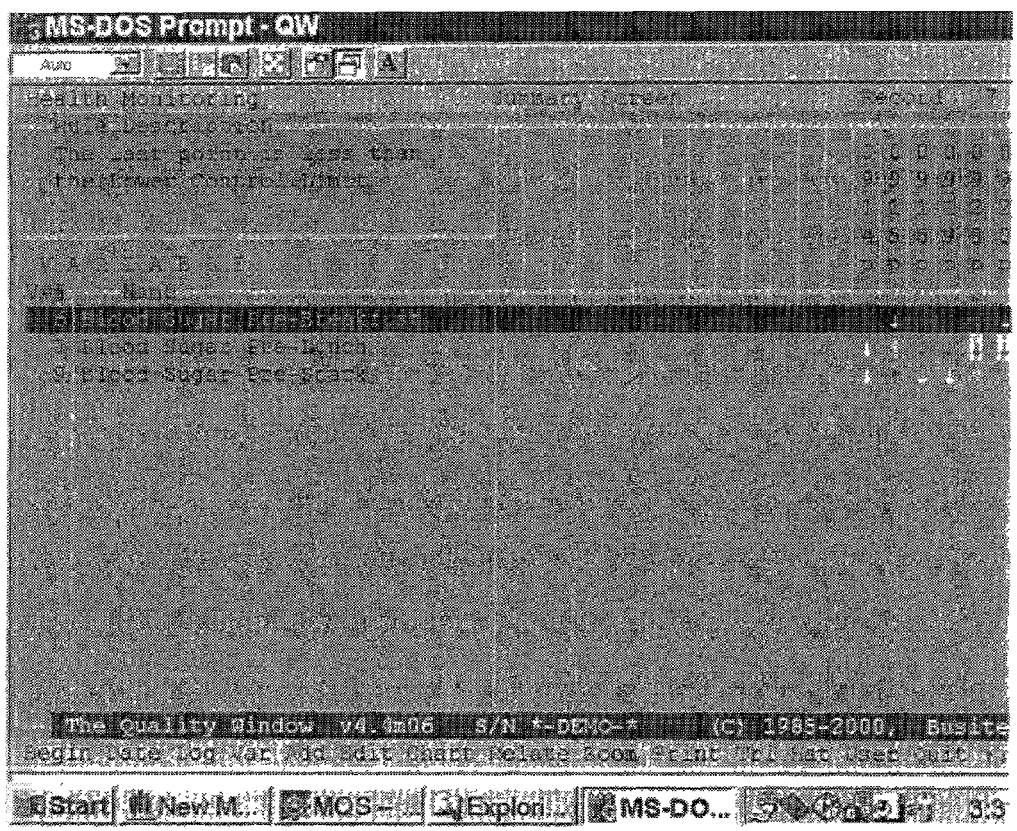
FIG. 5 depicts a summary screen suitable for a personal computer display or personal digital assistant (PDA) display.

The data analysis mechanism provides useful or actionable information for the improvement of an individual's health. Regardless of the type of data and the analysis performed upon it, the results of the analysis (i.e., the information) are preferably subsequently presented to the user (e.g., the individual or patient, caregiver, or medical professional) by an "information presentation mechanism". As used herein, an "information presentation mechanism" refers to any device, system, component, or output that communicates the information to the user. Non-limiting examples of information presentation mechanisms include various graphical or statistical outputs displayed on a computer, PDA screen, or paper, summary screens displaying health status via symbols, icons, diagrams, interpretation aids, alarms, and any other means of communicating status or recommendations. An exemplary summary screen suitable for a PC display or a PDA is shown in FIG. 5. For this summary screen, the color and/or symbol represent the location of the reading on the associated control chart. For instance, a red arrow pointing up may indicate a point outside the upper control limit.

Figure 6:
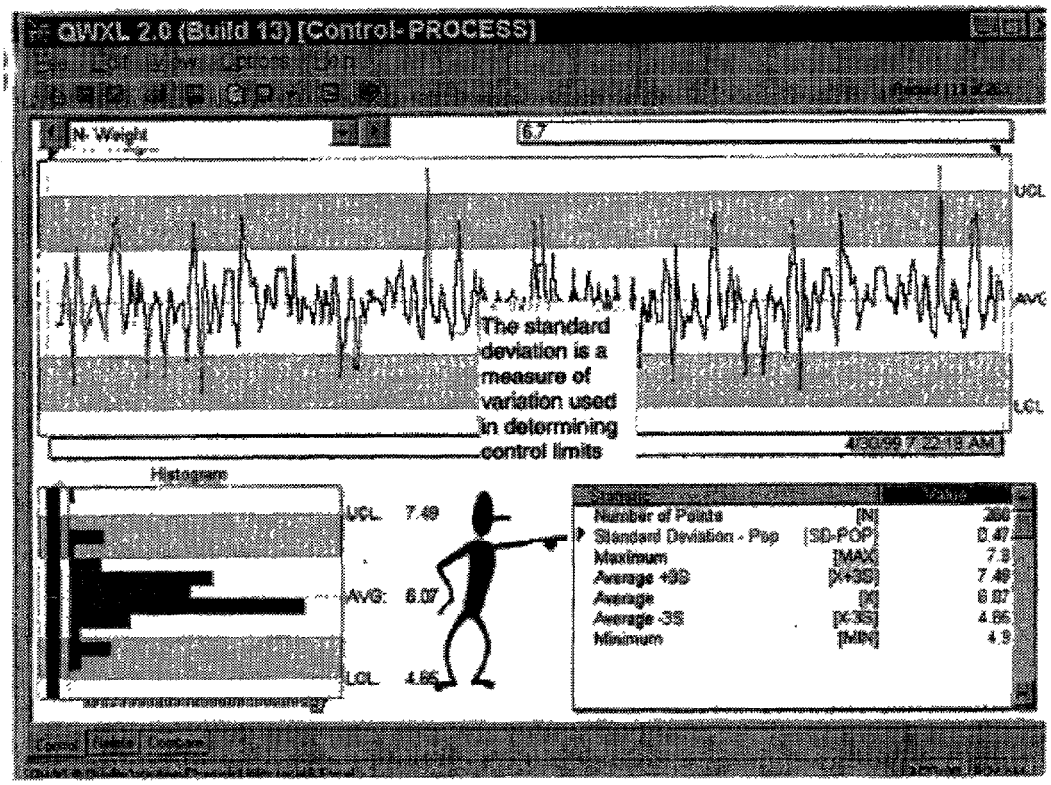
FIG. 6 depicts an exemplary anthropomorphic "guide" providing statistical information and including graphical "pointers" and pictorial icons used as interpretation aids.

Other symbolic means of representing the status of the individual's health or medical condition are also contemplated, including graphs, pie charts, geometric shapes, alphanumeric characters, icons depicting human expressions, etc. Interpretation aids may be graphical "pointers" or pictorial icons, such as anthropomorphic "guides" that highlight required or suggested interventions, such as out-of-control conditions, or which provide recommendations or conclusions in an easily interpreted manner. An exemplary anthropomorphic "guide" providing statistical information is shown in FIG. 6. The guide may optionally provide interpretive information, health tips, or indicate an auxiliary information source on the topic. In some embodiments, clicking on the icon or guide may automatically send the user (i.e., via a link) to more detailed data or analysis on the particular variable of interest. In particularly preferred embodiments, the guide may communicate via computer synthesized or stored speech (via any hardware/software as known in the art) indications of the need to intervene, definition of medical issues, or commendations or other medically useful feedback, such as the efficacy of a treatment or the identification of relationships between variables (e.g., relationships between weather patterns or activity level and asthma attacks).

In certain preferred embodiments, information, including alarms, may be communicated or automatically sent electronically to the individual or a medical professional. Information, including information related to the individual's disease states, may be sent automatically to the individual or patient (e.g., via the Internet) based on the individual's demographics, medical condition, or specific health events experienced by the individual. This information may include material on the causes, diagnosis, treatment, and/or prevention of a particular medical condition or health event experienced by the individual or related health events, medical conditions, or symptoms commonly experienced by others having similar demographics or medical conditions. The information may include URL-links to related websites, such as national research organizations or specific support groups relevant to the individual's medical condition or health event. Additionally, the information may comprise targeted advertising of products applicable to the prevention or treatment of the individual's medical condition or health event. For example, an individual with diabetes may automatically be sent information related to diabetes and its treatment and/or information or advertising for products related to diabetes, such as blood glucose monitors.

In certain alternative embodiments, the caregiver, individual, or patient may query (e.g., via e-mail, chat room, etc.) a specific population (e.g., one having the same medical condition, health event, demographics, etc., as the individual or patient), physicians, or research groups for advice or information regarding potential causes, remedies, services, and the like to allow them to develop an improved personal care plan. Further, the individual or caregiver may query a company or group of companies regarding their medical condition or health event and allow the company(ies) to provide details on any relevant products or services they can provide in order to allow the individual to make an informed selection from an expanded set of health improvement options. In order to ensure privacy, all data on individuals may be encrypted.

In certain alternative embodiments, the system of the present invention additionally comprises an "improvement implementation mechanism". As used herein, "improvement implementation mechanism" refers to any device, process, or system that enables the individual or caregiver to establish a protocol, preferably with a physician, to create or modify a treatment or treatment plan, preventive maintenance, or environmental plan or schedule to improve the individual's health. Several non-limiting examples include dietary plans (e.g., to help control a medical condition, such as high blood pressure or diabetes or to reduce weight, etc.); and a decision-tree to aid the individual in deciding which treatment(s) to use and under what conditions (e.g., a decision-tree on asthma treatments based on severity of symptoms and responses to various medications during an asthma attack or extended event). Others examples include a reminder system (automatic or manual) for therapeutic and/or preventative actions such as taking a medication or set of medications on a defined schedule, a confirmation system to facilitate recording therapeutic and/or preventative actions that have been taken, and an exercise regimen, to name a few. The treatment or improvement mechanism may function to aid the individual in scheduling the treatment, reminding the individual to undertake a treatment at prescribed intervals (i.e., increased treatment regimen compliance), or aid the individual in understanding their compliance to and/or the efficacy of the treatment regimen. The treatment or improvement to be implemented may be prescribed by a physician or may be defined based on population experience, advice from a support group or research organization, or from a company, such as a pharmaceutical or medical device company.

Figure 7:
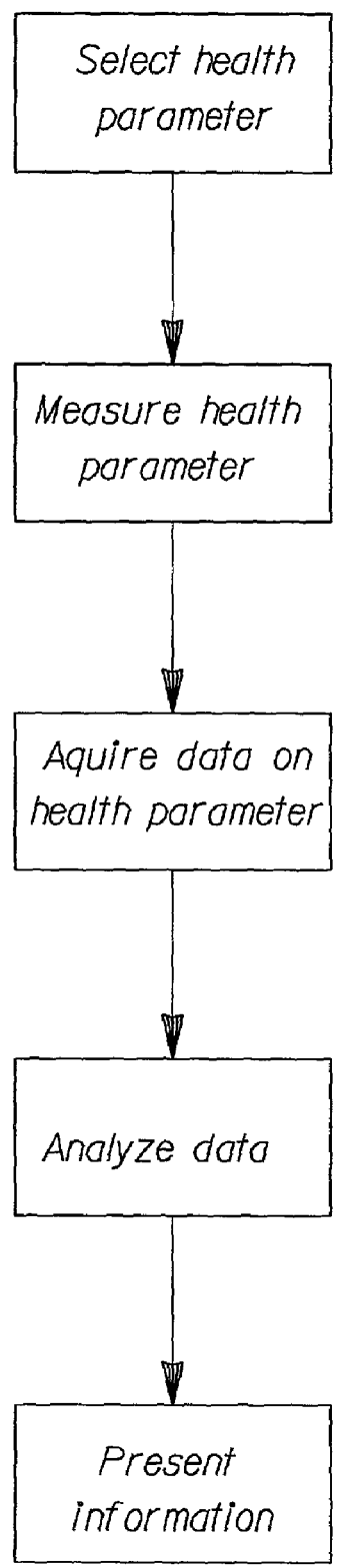
FIG. 7 depicts a flowchart outlining a method for improving the health of an individual.

The present invention also provides a method for improving the health of an individual. The method is outlined in the flow chart in FIG. 7 and comprises the steps of:

a) selecting health parameters, as described above, appropriate for the particular individual based on the individual's medical condition and history, any current or recent health event(s) of interest, the individual's age and/or demographics, or any other health parameter of interest to the individual, caregiver, or medical professional;

b) measuring the health parameters of interest and pertinent environmental or qualitative information to provide data via any of the approaches, sensors, or other means as described herein;

c) acquiring the data for storage and subsequent analysis via any data acquisition mechanism described above;

d) analyzing the data via any of the data analysis mechanisms, tools, or techniques described above to define out-of-control situations requiring intervention or potential causes of or remedies for a medical condition or health event; and e) presenting the information to the individual, caregiver, or medical professional via any of the information presentation mechanisms as described herein.

One preferred embodiment of the above method comprises the use of a tablet PC or wearable PC by a medical professional, such as a doctor or nurse, in a hospital or clinical environment to acquire, store, analyze, and download data from one or more patients and/or compare the patient to a relevant population or to historical data from said patient. In an especially preferred embodiment, data is entered into a tablet PC via speech recognition software running on the tablet PC. In other preferred embodiments, the system is made "hands-free" via use of wearable PCs, heads-up display glasses, etc.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for improving the management of an individual's asthmatic condition, comprising the steps of:
   a) identifying a failure event relating to the asthmatic condition;
   b) developing a treatment plan including at least one level of treatment indicated by a pre-defined change in the asthmatic condition;
   c) selecting at least one quantitative first variable related to the asthmatic condition, the failure event and the individual's health, for measurement and analysis;
   d) selecting at least two qualitative attributes related to the asthmatic condition and the individual's environment, for determination and analysis;
   e) developing a sampling strategy for measuring and/or determining the first variable and the at least two qualitative attributes at selected time(s) and frequency(ies);
   f) using a data measurement mechanism to measure the first variable at times and at a frequency according to the sampling strategy, to generate first data concerning the first variable;
   g) determining the at least two qualitative attributes at times and at a frequency according to the sampling strategy, to generate second data concerning the at least two qualitative attributes;
   h) assigning numerical values to the at least two qualitative attributes to adapt them to be treated as second and third variables;
   i) calculating a cumulative score from the at least two qualitative attributes, thereby converting the at least two qualitative attributes to a single fourth variable;
   j) using a data acquisition mechanism to store the first data and the second data on a storage medium;
   k) using a computer to analyze the first data and the second data, whereby the computer comprises software employing reliability engineering techniques; and
   l) using the computer to identify an environmental cause of the failure event;
   wherein the computer provides actionable information for the improvement of the individual's health by an information presentation mechanism, the actionable information including information relating to the environmental cause of the failure event.

2. The method of claim 1 further comprising the step of establishing control limits for the first variable and/or one or more of the second variable, third variable and fourth variable; defining an out-of-control condition relative the control limits for determination by the data analysis mechanism; tracking measurements or determinations of the first parameter and/or the one or more of the second variable, third variable and fourth variable against the control limits, and administering the at least one level of treatment when the out-of-control condition is presented.

3. The method of claim 2 further comprising the step of identifying best observed performance of the individual relative the first variable, and recalculating control limits based on the best observed performance.

4. The method of claim 1 further comprising the step of tracking time of failure events or time between failure events to provide information selected from the group consisting of: efficacy of the at least one level of treatment; effects of environmental conditions; and combinations thereof.

5. The method of claim 2 further comprising the step of establishing a target for the first variable, wherein the control limits are established relative the target.

6. The method of claim 5 further comprising the step of determining a capability ratio and using the capability ratio to determine efficacy of the treatment plan.

* * * * *

UNITED STATES PATENT AND TRADEMARK OFFICE
CERTIFICATE OF CORRECTION

| | | |
|---|---|---|
| PATENT NO. | : 7,835,925 B2 | Page 1 of 1 |
| APPLICATION NO. | : 10/078042 | |
| DATED | : November 16, 2010 | |
| INVENTOR(S) | : Roe et al. | |

It is certified that error appears in the above-identified patent and that said Letters Patent is hereby corrected as shown below:

Column 3

Line 38, delete "fixture" and insert --future--.

Signed and Sealed this
Thirtieth Day of August, 2011

David J. Kappos
*Director of the United States Patent and Trademark Office*